US010474793B2

(12) United States Patent
Aristizabal et al.

(10) Patent No.: US 10,474,793 B2
(45) Date of Patent: Nov. 12, 2019

(54) SYSTEMS, APPARATUS AND METHODS FOR DELIVERY AND AUGMENTATION OF BEHAVIOR MODIFICATION THERAPY AND TEACHING

(71) Applicant: Northeastern University, Boston, MA (US)

(72) Inventors: John Aristizabal, La Jolla, CA (US); Mitul Shah, La Jolla, CA (US); Asim Mittal, La Jolla, CA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 13/917,425

(22) Filed: Jun. 13, 2013

(65) Prior Publication Data

US 2014/0370470 A1    Dec. 18, 2014

(51) Int. Cl.
*G06F 19/00* (2018.01)
*A61B 5/16* (2006.01)
*A61B 5/00* (2006.01)
*A61B 5/11* (2006.01)

(52) U.S. Cl.
CPC ............ *G06F 19/3418* (2013.01); *A61B 5/16* (2013.01); *G06F 19/3481* (2013.01); *A61B 5/0022* (2013.01); *A61B 5/0059* (2013.01); *A61B 5/11* (2013.01); *A61B 5/4836* (2013.01)

(58) Field of Classification Search
CPC . A63B 24/0003; G06F 19/3481; G06F 19/00; G06F 19/3418; A61B 5/0059; A61B 5/11; A61B 5/16; A61B 5/4836; A61B 5/0022
See application file for complete search history.

(56) References Cited

U.S. PATENT DOCUMENTS

| 6,056,671 | A  | 5/2000  | Marmer         |
| 6,685,480 | B2 | 2/2004  | Nishimoto et al. |
| 7,308,112 | B2 | 12/2007 | Fujimura et al. |
| 7,433,024 | B2 | 10/2008 | Garcia et al.  |
| 8,306,635 | B2 | 11/2012 | Pryor          |
| 8,322,856 | B2 | 12/2012 | Vertegaal et al. |
| 8,405,706 | B2 | 3/2013  | Zhang et al.   |

(Continued)

FOREIGN PATENT DOCUMENTS

WO    WO 2011/119233 A1    9/2011

OTHER PUBLICATIONS

Anderson, et al, "Lean on Wii: Physical Rehabilitation With Virtual reality and Wii Peripherals", Annual Review of Cybertherapy and Telemedicine 2010, IOS Press, 2010, ISBN: 1607505606, pp. 229-234.

(Continued)

*Primary Examiner* — Timothy A Musselman
(74) *Attorney, Agent, or Firm* — Verrill Dana, LLP

(57) ABSTRACT

A system, apparatus and method for providing a lesson to a user of the system. The lesson may be a behavioral lesson or a teaching lesson, such as where knowledge or skill is being imparted to the user. In one aspect, the inventions include a sensor apparatus, the sensor apparatus generating an output indicative of a user's actions. Memory is provided for storing an individual user profile including at least a plan and a display. A processor and associated storage comprising a computing platform to generate user feedback.

19 Claims, 2 Drawing Sheets

(56) References Cited

U.S. PATENT DOCUMENTS

| | | | |
|---|---|---|---|
| 8,535,130 B2 | 9/2013 | Ciarrocchi | |
| 9,122,053 B2* | 9/2015 | Geisner | G02B 27/017 |
| 9,218,063 B2* | 12/2015 | Galor | G06F 3/017 |
| 2004/0230549 A1 | 11/2004 | Freer et al. | |
| 2006/0040248 A1* | 2/2006 | Aaron | G09B 7/00 434/362 |
| 2006/0281977 A1 | 12/2006 | Soppet | |
| 2008/0191864 A1 | 8/2008 | Wolfson | |
| 2009/0252423 A1 | 10/2009 | Zhu et al. | |
| 2009/0318775 A1 | 12/2009 | Michelson et al. | |
| 2009/0325141 A1* | 12/2009 | Kelly | G09B 7/00 434/362 |
| 2010/0112533 A1* | 5/2010 | Chan et al. | 434/250 |
| 2010/0164956 A1* | 7/2010 | Hyndman | G06F 3/011 345/427 |
| 2010/0199228 A1 | 8/2010 | Latta et al. | |
| 2011/0054870 A1 | 3/2011 | Dariush et al. | |
| 2013/0078600 A1 | 3/2013 | Fischer et al. | |
| 2013/0198625 A1* | 8/2013 | Anderson | G06F 3/016 715/701 |
| 2013/0309641 A1 | 11/2013 | Sawyer et al. | |
| 2014/0147820 A1* | 5/2014 | Snow | G06F 19/3481 434/247 |
| 2014/0168378 A1* | 6/2014 | Hall | H04N 13/0246 348/47 |
| 2014/0205986 A1* | 7/2014 | Pillay | G09B 7/02 434/335 |
| 2014/0212854 A1* | 7/2014 | Divakaran | G09B 19/00 434/236 |
| 2014/0272908 A1* | 9/2014 | Black | G09B 5/08 434/362 |
| 2015/0023557 A1* | 1/2015 | Yoo | G06K 9/6282 382/103 |
| 2015/0079565 A1* | 3/2015 | Miller | G09B 23/281 434/252 |
| 2015/0099255 A1* | 4/2015 | Asian | G09B 5/08 434/350 |

OTHER PUBLICATIONS

Chen, et al., "Networking Telemedicine in Portable Rehabilitation Robot Monitor System", Journal of Applied Information Technology, vol. 3, No. 1, 2007, 7 pages.

Cook, "Microsoft Picks 11 Startups for new Kinect Accelerator" http://www.qeekwire.com/2012/Microsoft-names-11-startups-kinect-accelarator /, Apr. 2, 2012, 6 pages.

Lakeside Center for Autism, "Technology" http://www.lakesideautism.com/technoloqv/ 2012, 3 pages.

Lakeside Center for Autism, "Kinetix Academy Begins!", http://www.lakesideautism.com/2012/05/20/kinetix-acaderny-begins/, May 20, 2012, 6 pages.

Lakeside Center for Autism, "We Did It!", http://www.lakesideautism.com/2012/05/21/we-did-it/, May 21, 2012, 4 pages.

Nosowitz, "Using the Microsoft Kinect to Detect Autism", www.popsci.com/technology/article/2012-05/using-microsoft-kinect-detect-autism, May 8, 2012, 3 pages.

Toppo, "Video Games Help Autistic Students in Classrooms", http://www.usatoday.com/news/health/story/2012-05-31/video-games-autism-students/55319452/1, Jun. 1, 2012, 4 pages.

Woodward, "Microsoft's Kinect Accelerator: The Real Scoop on the Lucky Few", http://wwwxconomy.com/seattle/2012/04/02/microsoft-kinect-accelerator-teams/ , Apr. 2, 2012, 5 pages.

Young, "Motion Sensors in Physical Therapy", Norwegian University of Science and Technology Department of Computer and Inforamation Science, Dec. 2010, 108 pages.

International Search Report, PCT/US2014/041384, dated Mar. 10, 2015.

* cited by examiner

Single-User Scenario
For delivery of therapy to patient or caregiver training

Multi-User Scenario Locally
Can include therapist, caregiver or patient

Multi-User Scenario Remotely
Can include therapist to patient, or patient to patient

SYSTEMS, APPARATUS AND METHODS FOR DELIVERY AND AUGMENTATION OF BEHAVIOR MODIFICATION THERAPY AND TEACHING

FIELD OF THE INVENTION

Systems, apparatus and methods provide for delivery and augmentation of a user's actions. More particularly, they provide for the delivery and augmentation of behavior modification therapy and teaching through an attentive computing platform to enable interaction with therapeutic and or teaching applications.

BACKGROUND OF THE INVENTION

Autism Spectrum Disorder (ASD) is characterized by severe and pervasive impairment in several areas of development: social interaction, communication and the presence of stereotyped behavior, interests, and activities. Autism Spectrum Disorders include Autistic Disorder, Asperger's Syndrome, Pervasive Development Disorder Not Otherwise Specified (PDD-NOS), and Childhood Disintegative Disorder. An individual classified as autistic shows delays in the development of social interaction, verbal and nonverbal communication and stereotyped behaviors, interests, and activities. Nonverbal communication represents two-thirds of all communication and facilitates social interaction. Examples of non-verbal behaviors in social interaction include eye contact or gaze, facial expression, gestures, body language and posturing. Asperger's Syndrome differs from other autism spectrum disorders by its relative preservation of linguistic and cognitive development. It is much like autism in that those affected may have difficulty picking up on social cues, body language, and speech pitch and tone, and they may have difficulty overall with social situations. Other similarities include dislike of routine changes, fixation or hyper focus on specific interests, talking a lot and about only their own interests, and increased sensitivity of one or more of the five senses. The Center for Disease Control and Prevention estimates that an average of 1 in 88 children in the U.S. has ASD.

Although there is no cure, autism is treatable and symptoms associated with autism often improve as children start to acquire language and learn how to communicate their needs. Early intensive treatment may allow for relatively normal development in the child and reduce undesirable behaviors. Applied early and intensively enough, studies have shown that as many as 50% of autistic children participating in such programs can be referred back to normal schooling and education. Available treatments for autism may include a combination of the following therapies: applied behavior analysis (ABA), structured teaching, speech and language therapy, social skills therapy, and occupational therapy. Autism therapies attempt to lessen the deficits and abnormal behaviors associated with autism and other autism spectrum disorders (ASD), and to increase the quality of life and functional independence of autistic individuals, especially children. Treatment is typically tailored to the child's needs. Training and support are also given to families of those with ASD.

Applied Behavior Analysis (ABA) is a scientifically proven evidence based approach to treating Autism and has become widely accepted among health care professionals and used in many schools and treatment clinics. ABA encourages positive behaviors and discourages negative behaviors in order to improve a variety of skills. The child's progress is tracked and measured. The gold-standard treatment for autism involves 30 to 40 hours per week of one-on-one work with a trained therapist.

Despite these evidence based treatment solutions a number of serious problems remain. First, ABA is very expensive. The recommended number of hours for intensive behavioral intervention is 25-40 hours per week of one-on-one therapy for two to three years. In some cases the costs are fully or partially covered by insurance, schools or state and federal programs, but in many cases it is not and requires the caregivers to pay for therapy directly out of pocket. Second very few people receive the recommended number of hours, the vast majority receive much less if any. Third, with the increase in diagnosis, availability of board certified therapist in metropolitan areas is becoming difficult while in rural areas it is severely lacking. Fourth, ABA therapists may be poorly trained or untrained. While top therapists have embraced naturalistic ABA therapy, flexible approaches to building emotional engagement, and other child-appropriate techniques, many ABA therapists are trained only in "discrete trials." Discrete trials, which involve repeated attempts to get a child to respond appropriately, are appropriate in limited circumstances—and certainly not for 40 hours a week.

Additionally, other motion tracking platforms in the form of commercially available accelerometer enabled or augmented motion tracking gaming systems, such as the Kinect system from Microsoft, have been used in a supervised rehab setting by allowing patients to participate in entertainment programs specific to the gaming platform.

Various attempts have been made to integrate interactive technologies into a useful tool for aiding in these efforts. For example, the Lakeside Center for Autism has utilized various touch screen technologies to support participation and learning. The University of Minnesota's Institute of Child Development has recently used the Microsoft Kinect motion detection system to monitor students, to look for signs of unusual behavior that might suggest potential ASD. Yet other vision based activity recognition and monitoring systems have been proposed for guided virtual rehabilitation. See, e.g. Dariush et al. US published patent application US 2011/0054870, hereby incorporated by reference. The system follows the sequence of providing instructions for guided movement, capture of the subject's movement, tracking the movements on an Avatar, calculation of biomechanical quantities, and providing feedback to the patient.

Despite these prior efforts and suggestions, no comprehensive or fully effective system has been proposed previously. The systems, apparatus and methods of the present inventions seek to remedy some or all of the shortcomings of the prior systems.

BRIEF SUMMARY OF THE INVENTION

The inventions provide for a system, apparatus and methods for providing a lesson to a user of the system. The lesson may be a behavioral lesson or a teaching lesson, such as where knowledge or skill is being imparted to the user. In one aspect, the inventions include a sensor apparatus, the sensor apparatus generating an output indicative of a user's actions. Memory is provided for storing an individual user profile including at least a plan and a display. A processor and associated storage comprising a computing platform to generate user feedback such as by the following steps. First, selecting an application lesson based at least in part on the individual user profile, the application lesson adapted to elicit a desired user response. Second, generating an application lesson display for presentation to the user to elicit the selected user response. Third, displaying the application lesson to the user. Fourth, comparing the user response via the output from the user tracking apparatus with the desired user response. Fifth, perform feedback analysis to determine the effect of the lesson. Sixth, generating a second display for presentation to the User to elicit the selected user behavior.

In one application, this system, apparatus and method is adapted for the delivery and augmentation of behavior modification therapy through an attentive computing platform that detects a user's physical actions, gestures, body orientation, eye-gaze direction, facial expressions, level of engagement, both verbal and non-verbal responses, physiological measurements such as heart rate and respiration rate for the purpose of enabling interaction with therapeutic applications and or teaching applications. Behavior modification therapy is used to teach individuals with developmental disabilities, behaviors, skills and educational lessons they demonstrate deficiencies in. An incorporated software platform provides access to specially designed, therapeutic applications geared toward teaching and developing necessary behaviors and skills. Behaviors and skills taught include, but are not limited to: receptive language, expressive language (mands, tacts, intraverbals, etc.), echoics, nonverbal communication skills (joint attention, eye-contact, facial expression, body language) social skills, motor imitation, self-help skills, etc.

A standard developmental assessment and or treatment plan identifies deficiencies in behaviors, skills and education as compared to typically developed individuals. Once the behaviors, skills and educational lessons that need to be taught are identified, those behaviors are dissected into smaller lessons and incorporated into a therapy application, allowing for easier learning and tracking of progress. The user is allowed multiple opportunities to practice such skills through the system-delivered therapy applications and games.

Based on a preference assessment and the individual's likes, the software platform can deliver a plurality of games, visual and audio media, visual and verbal praise and preferred activities on the platform to be used as positive reinforcement to motivate continuation of the therapeutic lesson and upon completion of a therapeutic lesson.

In conjunction with the software, the system uses a sensor suite preferably including, but not limited to, motion tracking sensors, active infrared sensors, facial feature recognition, eye tracking, voice recognition and wearable body sensors to register a user's response and provide pertinent feedback and instruction.

The feedback and instructional cues will be referred to as prompting. Prompts are specific cues to the individual user intended to elicit a particular correct response. Prompts serve to strengthen the association between a particular instruction, event, or circumstance and the desired response and are intended to ensure a correct response. The type and level of prompting needed, is determined by user need and preference as some individuals will respond more positively to a particular type of prompting. Software algorithms can track which prompting method is more effective for the user by measuring and tracking, but not limited to: reaction rate, response time, heart rate variability, engagement levels, emotional status, and time to skill acquisition. Using the same measuring and tracking algorithms as above the system also adaptively adjust to the learning rate of the user and either decrease or increase prompting to the user as the user improves or begins new lessons too quickly. The system tracks progress being made and will adaptively remove and fade the prompts until the user has mastered the criteria provided and no prompting is required. This is presented to the user through a computer system or gaming platform and a display device.

The sensor suite and software algorithms will also track the uses attentive status and engagement levels by measuring and tracking, but not limited to: body orientation, eye gaze direction, vocal responses, response time, and heart rate variability. If the system detects a loss in attention or engagement it may provide any combination of vocal prompts, visual prompts and intermittent introduction of the positive reinforcement to regain the user's attention thereby redirecting and providing continuation of the therapeutic lesson.

The system can track progress on multiple behaviors and skills as they are mastered and subsequently chain these together into more complex behaviors and skills, which are then practiced in a therapy application targeting the more complicated behavior or skill. Behavior chains are effective procedures for teaching children with autism a variety of multi-step skills, including self-help activities, vocational skills, and communication. The system will also reintroduce mastered skills and lessons to ensure retention and maintenance of that skill or lesson.

The system optionally can identify individual users based on physical attributes via facial and voice recognition even when multiple users are using the system simultaneously. Depending on the therapy or teaching module, self-representation of the user on the display device may take the form of but not limited to a mirror image of themselves, a more abstract representation such as an outline or shadow or an avatar representation of that is controlled by each individual.

During social therapy lessons the system can prompt and teach subtle nonverbal cues of human interaction and skills for effective verbal and nonverbal communication. To facilitate the teaching of social behaviors and skills, it may accommodate multiple users concurrently, either locally or remotely in any combination, allowing for therapist and caregivers to he active participants in some of the therapy applications regardless of location. Remote therapy functionality can be used within an active therapy lesson or separately as a remote face to face consultation between individuals. These multi-user scenarios can occur via a user-controlled avatar or live video of the individual. This remote participation will also allow for a social network of approved participants to participate in therapy sessions when remote participation facilitates therapy goals. This social networking component will also allow for information exchange and sharing of therapeutic techniques, creating a virtual community of users targeting specific behavioral goals. This community can have interactions and information exchanges such as: caregiver-to-caregiver or caregiver-to-therapist or therapist-to-developmental delayed individual. This virtual community will allow for dissemination of information as well as interaction with individuals outside the core care group, further educating caregivers and therapists about treatment and providing the developmentally delayed individual more opportunities to safely interact both socially and therapeutically with others.

The platform allows integration of real world objects that can he identified by the sensor suite; further augmenting and promoting generalization of skills learned within the system and expanding them to real world usage. An exemplar of this would be once a receptive language lesson of object identification is mastered on the software platform the system would request the user find that object in the physical world and hold it to be identified by the sensor suite. Another exemplar would be the inclusion of PECS (Picture Exchange Communication System) which uses pictures instead of words to help children communicate. The PECS picture cards or other type of flash cards would be identified by the sensor suite held up. The system would also be able to identify visual schedules which are a set of pictures that communicates a series of activities or the steps of a specific activity. Visual schedules are meant to help children understand and manage the daily events in their lives. The system could both display the schedule as well as identify when an element of the schedule is held by the child and either initiate a specific action or lesson by the system or identify an action as completed.

All progress data is tracked, sent and stored into a centralized database, accessible via a portal to the caregiver and therapist to review as well as for data analysis and continued customization of lessons. Because of the system's ability to record different response characteristics the system will also allow for more precise measurement of a user's behavior and skills automating the progress tracking of such behaviors by a therapist or caregiver. The system will also allow for video recording of behaviors for a therapist to perform a functional behavioral analysis. Video of the user is cached on system memory so if the antecedent to a specific behavior needs to be reviewed to understand what caused such behavior, a therapist or caregiver can request that the system tracks that behavior or skill and have video prior to the behavior to review for further analysis.

The system will also provide lessons and appropriate intervention techniques for therapist and caregiver training that coincide with the lessons that the developmentally delayed individual is learning. The lessons and training will allow the therapist and caregiver to learn and practice techniques to enhance their child's social-communication skills and learning. If the lessons or skills being taught to the child are social in nature the system will guide the caregiver or therapist with appropriate intervention techniques. Behaviors and skills the system could guide the teaching of include but are not limited to: social engagement, turn-taking, language, imitation and play skills.

DETAILED DESCRIPTION OF THE INVENTION

Figure 1:
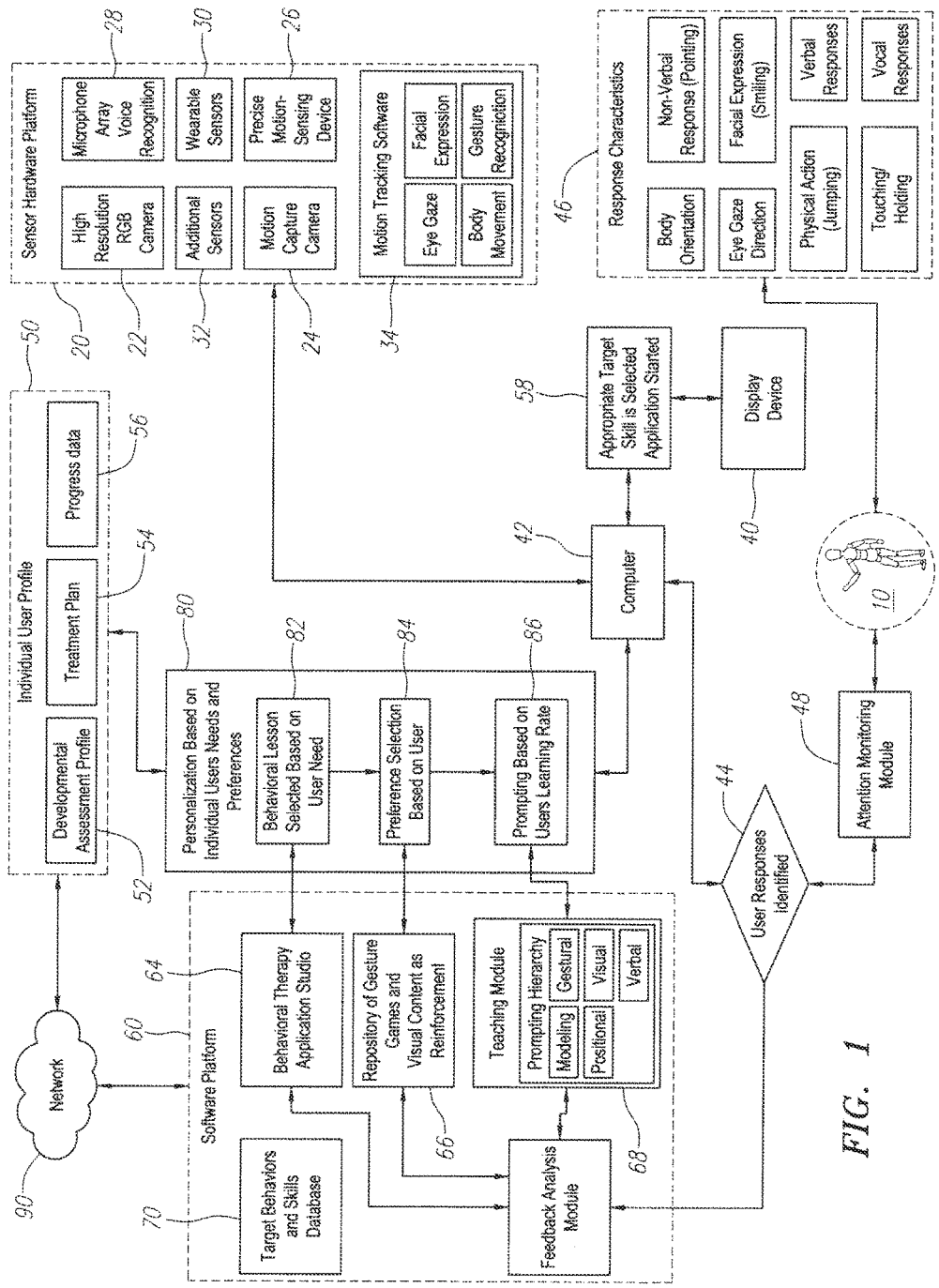
FIG. 1 is a schematic and functional block diagram of the system and apparatus, for performing the methods herein.

FIG. 1 provides a block schematic and functional overview of key components of the system. The system consists of several key components. It will be appreciated by those skilled in the art that the functionalities identified here may be achieve by any form of computer hardware and software, and that the placement of a particular element in the Figure is not limiting in terms of implementation. Interconnection of the various functionalities and components may be by any form of communication system or network 90.

A user 10 interacts with the system and apparatus described herein. The system includes a sensor platform 20. Preferably, the components of the sensor system include both visual sensing and audio sensing. Various types of visual sensing may be utilized. For example, a high resolution camera 22, such as a full color Red Green Blue (RGB) camera, may be used. Optionally, a motion capture camera 24, such as a still frame camera or freeze frame camera may be used. For certain applications, a precise motion sensing device 26 may be used. Sound sensing is optionally utilized, such as via a microphone, more preferably a microphone array 28, preferably adapted for voice recognition. Any form of additional sensors may be utilized consistent with the goals and objectives of this invention, such as wearable sensors 30, e.g., motion detection sensors, gyroscope sensors, balance sensors, etc. Various additional sensors 32 may be employed. Various sensor systems, such as motion tracking systems, may include motion tracking hardware, motion tracking software, a camera system, a microphone array and additional sensors. Systems known to those skilled in the art include the Kinect system from Microsoft, the PrimeSense platform, or a system of one or more cameras coupled with motion tracking software. The motion tracking apparatus may either be with or without a depth sensor. The depth sensor preferably consists of an array of cameras and structured light that is able to image and assess the environment and discreet objects within three-dimensional space within its field of view. Objects within that field of view can be assigned a depth and size that can be forwarded to software algorithms for the purposes of enabling automatic identification based upon pre-existing algorithms. In addition to measuring depth, the depth sensor is also equipped with a video camera and microphone array to enable video recording and voice/sound recognition.

A display 40 interfaces with the user 10, A standard display in the form of a computer monitor, television, projector or virtual reality head mounted display can be used to view the output from the clinical software platform and the depth sensors. Optionally, a display showing three dimensional (3D) images may be utilized to provide a more realistic appearance, such as of the avatar. Touch screen capability may be included. The display 40 preferably includes audio output capabilities. System computer 42 serves to coordinate and process the various functions described herein. The user 10 interfaces with the overall system in a closed loop manner via the sensor platform 20 as input of user 10 information, which is processed as described herein, and an output is provided back to the user 10 via the display 40. The display 40 may display a graphical user interface to permit user interaction with the system. For certain applications, particularly for autism related applications, it may be preferable to have a system that does not require the user 10 to interact with the display or other input device, but rather, operate in a natural way such as would be the case when interacting between two humans. Towards that end, users 10 may interact with the system using either voice navigation and/or motion gestures which can be tracked with the depth sensor, or other analysis software designed to determine the user's desire.

The output of the various sensors 20 is analyzed for response characteristics, such as at decision block 44. Any form response characteristic 46 may be discerned. These include, but are not limited to: body orientation, eye gaze direction, facial expression, such as smiling, physical action, such as jumping, touching and or holding, verbal response, non-verbal response (such as pointing) and vocal response. While optionally based on the various responses identified previously, an attention monitoring module 48 is identified as a status or state of the user 10.

An individual user profile 50 is provided and stored in memory. The individual user profile 50 may be input via a user of the system who is providing the lesson, therapy or instruction, or may be generated by the system based upon information obtained from databases or other observations via the sensor platform 20. A developmental assessment profile 52 identifies the status of a particular user of the system, identifying capabilities, strengths and weakness, problematic behaviors, important skills lacking, and preferences. A treatment plan 54 is defined. Progress data 56 is stored on an individual user basis. An appropriate target skill is selected 58 and the application is started. Optionally, the target skill or task may be subdivided into smaller tasks.

A platform 60 provides analysis of the sensed data. A feedback module 62 collectively analyzes the various input data to determine the output to provide to the user, based on the various factors and methods described herein. An application 64, such as a teaching application or behavioral therapy application studio, provides for various modes of interaction with the user 10. A teaching module, also referred to as a prompt or prompting module, selects the mode or modes of interaction. For example, the teaching or prompting may include one or more of the following: modeling, gestural, positional, visual and verbal. Prompting is a planned teaching strategy. In one aspect, the system identities specific cues to the individual that elicits a particular correct response. A reinforcement module 66 selects and presents a positive reinforcement. Modes of reinforcement vary based on the user and application. Examples include gesture games, or forms of visual content, such as characters, avatars, or the like. Optionally, a target skills database, such as a teachable information or skills database or target behaviors and skills database is provided. As skills are learned, more skills may be joined or chained together into more complex behavior.

A personalization module 80 is preferably included, so as to personalize or tailor the application, teaching or therapy to the user 10. The user need 82 may be an identified area to be taught or a behavioral lesson selected based on user need. Optionally, a preference selection based on the user 84 may be employed. Prompting or teaching may be based on the user's learning rate 86.

Figure 2:
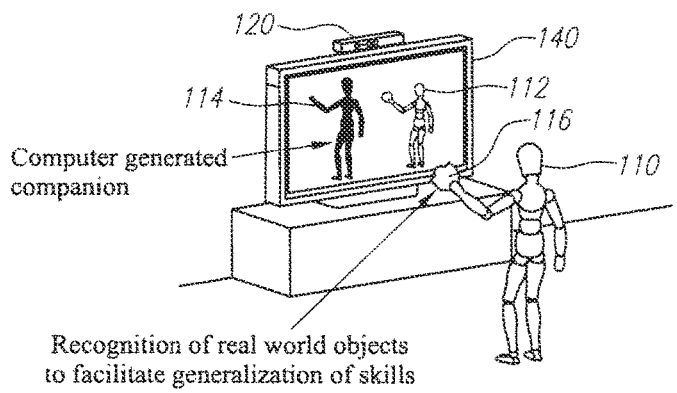
FIG. 2 is an exemplary image display and contextual setting of a single-user scenario.

FIG. 2 is an exemplary image display and contextual setting of a single-user scenario. The user 110 is located within the field of the sensor unit 120, and receives information on the display 140. A user image 112 may he displayed on the display 140. The image may be a realistic dynamic photographic image, typically a mirror image. Optionally, the image may be displayed within a mirror type frame. Alternately, the image may be abstract, such as an outline or silhouette. Alternately, the image may be an avatar, either chosen by the user or by the system. Optionally, the display may depict objects with which the user 110 may appear to interact. Additional images 114, such as of a teacher or therapist, may be displayed. Structures 116 in the physical world may be detected and displayed on the display 140.

Figure 3:
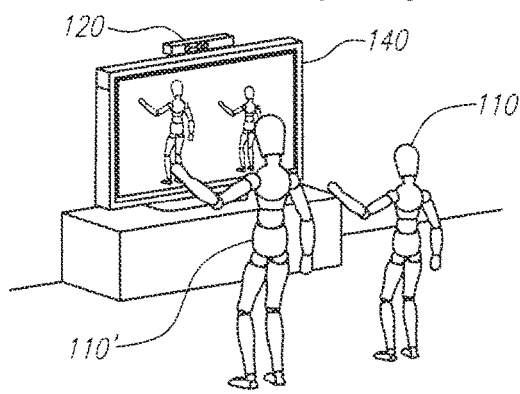
FIG. 3 is an exemplary image display and contextual setting of a local multi-user scenario.
Figure 4:
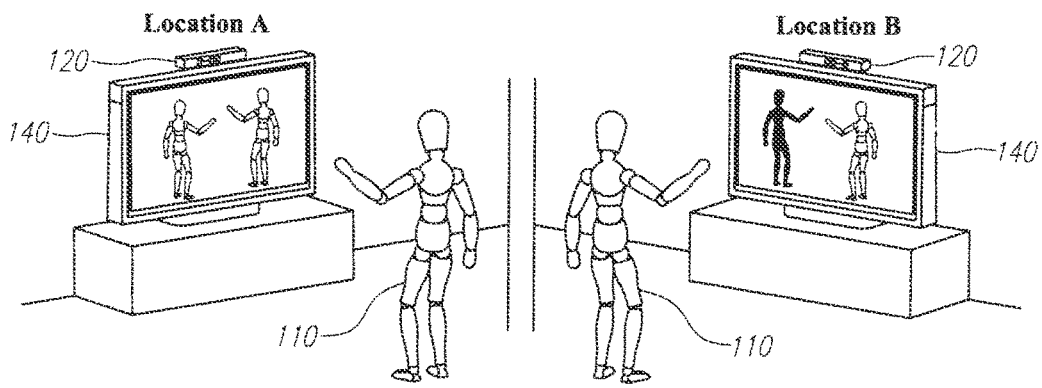
FIG. 4 is an exemplary image display and contextual setting of a remote multi-user scenario.

FIGS. 3 and 4 show multi-user scenarios. The system has common components to FIG. 2, and are similarly numbered. The images of a first user 110 and a second user 110' may be displayed on the display 140. In the case of FIG. 3, both users are within the field of a single sensor 120. In the case of FIG. 4, the users are separated, typically at locations remote from one another, and are within fields of different sensors, a first sensor 120 and a second sensor 120'. The forms of images may be as described in connection with FIG. 2, above.

All publications and patents cited in this specification are herein incorporated by reference as if each individual publication or patent application were specifically and individually indicated to he incorporated by reference. Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the following claims.

What is claimed:

1. A system for providing a lesson to a user with an autism spectrum disorder to teach communication skills or behaviors, comprising:

a sensor apparatus, the sensor apparatus generating an output indicative of a user's actions, the sensor apparatus including a visual sensor having a field of view directed toward the user and comprising a depth sensor operative to image and assess discreet objects, picture cards, or structures within a three-dimensional space with which the user appears to interact within the field of view, the sensor apparatus operative to assign a depth and size to the object, picture card, or structure, the sensor apparatus further including a motion tracking sensor, facial feature recognition, eye tracking, and voice recognition, memory for storing an individual user profile including at least a developmental assessment profile, a treatment plan, and progress data, an image display, and a processor and associated storage comprising a computing platform in communication with the sensor apparatus, the memory, and the image display, the computing platform including:

(i) a personalization module in communication with the individual user profile and operative to identify a communication skill or behavioral lesson based on user need, (ii) a feedback module, and (iii) a prompting module in communication with the feedback module and the personalization module, and operative to select modes of interaction including modeling, gestural, positional, visual, and verbal modes of interaction;

the computing platform operative to generate user feedback and reinforcement of a communication behavior or skill by:

(a) selecting an application lesson based at least in part on (1) the developmental assessment profile and (2) application of the personalization module to customize the lesson based at least in part on a user's preference stored in the individual user profile, the application lesson adapted to elicit a desired user response to teach verbal and non-verbal communication skills or behaviors, (b) generating a display of an application lesson for presentation to the user to elicit the desired user response, the application lesson including picture cards having pictures thereon for communication, (c) displaying the application lesson to the user on the image display, including requesting the user to find one of the picture cards having a picture thereon for communication, and to hold the picture card to be identified;

(d) receiving from the sensor apparatus a user response, the user response including holding the picture card for imaging by the sensor apparatus, (e) analyzing at the feedback module the user response to identify the picture on the picture card and to discern response characteristics of the user, including the user's eye gaze direction, facial expression, body orientation, verbal response, and response time, (f) comparing the user response with the desired user response, including identifying the picture on the picture card held by the user, (g) performing feedback analysis to determine the effect of the lesson, including determining the user's attentive status and initiating a specific action or lesson in response to identification of the picture on the picture card held by the user, (h) generating a prompt to regain the user's attention, (i) generating a second display on the image display for presentation to the user to elicit the desired user response; and (j) tracking which prompting method is more effective for the user by measuring and tracking reaction rate, response time, engagement level, emotional state and time to skill acquisition.

2. The system for providing a lesson to a user of the system of claim 1 wherein the lesson is a behavioral lesson or a teaching lesson.

3. The system for providing a lesson to a user of the system of claim 1 wherein the individual user profile further includes a teaching plan.

4. The system for providing a lesson to a user of the system of claim 1 wherein the sensor apparatus includes sound sensing including a microphone or microphone array adapted for voice recognition.

5. The system for providing a lesson to a user of the system of claim 1 wherein the personalization module utilizes the user's learning rate in part to generate the lesson.

6. The system for providing a lesson to a user of the system of claim 1 further including an attention monitoring module.

7. The system for providing a lesson to a user of the system of claim 1 further including a social networking module.

8. The system for providing a lesson to a user of the system of claim 1 further including a reinforcement module operative to select and present a positive mode of reinforcement including a gesture game, visual content, audio content, verbal praise, and a preferred activity.

9. The system for providing a lesson to a user of the system of claim 1 further including a response characteristics module.

10. The system for providing a lesson to a user of the system of claim 1, wherein the depth sensor comprises an array of cameras.

11. The system for providing a lesson to a user of the system of claim 10, wherein the depth sensor further comprises structured light.

12. The system for providing a lesson to a user of the system of claim 1, wherein the sensor apparatus includes a motion tracking apparatus, the motion tracking apparatus including the depth sensor, and the motion tracking apparatus is operative to track motion gestures of the user.

13. The system of claim 1, wherein the computing platform is further operative to generate user feedback and reinforcement of a behavior or skill by tracking progress made by the user and adaptively removing and fading prompts until the user has mastered a skill or behavior and no prompting is required.

14. The system of claim 1, wherein:
the sensor apparatus further includes a wearable body sensor;
step (e) further comprises analyzing at the feedback module heart rate variability of the user; and
step (j) further comprises measuring and tracking heart rate variability.

15. The system of claim 1, wherein the computing platform further includes a database of target behaviors and skills including receptive language, expressive language, echoics, nonverbal communication, and motor imitation.

16. The system of claim 1, wherein the computing platform is further operative to generate user feedback and reinforcement of a behavior or skill by:

(k) adaptively adjusting to a learning rate of the user by decreasing or increasing prompting to the user as the user improves or begins a new lesson too quickly.

17. A system for providing a lesson to a user with an autism spectrum disorder to teach communication skills or behaviors, comprising:

a sensor apparatus, the sensor apparatus generating an output indicative of a user's actions, the sensor apparatus including a visual sensor having a field of view directed toward the user and comprising a depth sensor operative to image and assess discreet objects, picture cards, or structures within a three-dimensional space with which the user appears to interact within the field of view, the sensor apparatus operative to assign a depth and size to the object, picture card, or structure, memory for storing an individual user profile including at least a developmental assessment profile, a treatment plan, and progress data;

an image display; and a processor and associated storage comprising a computing platform in communication with the sensor apparatus, the memory, and the image display, the computing platform including:

(i) a personalization module in communication with the individual user profile and operative to identify a communication skill or behavioral lesson based on user need, (ii) a feedback module, and (iii) a database of target communication behaviors and skills including receptive language, expressive language, echoics, nonverbal communication, and motor imitation;

the computing platform operative to generate user feedback and reinforcement of a communication behavior or skill by:

(a) selecting an application lesson based at least in part on (1) the developmental assessment profile and (2) application of the personalization module to customize the lesson based at least in part on a user's preference stored in the individual user profile, the application lesson adapted to elicit a desired user response to teach verbal and non-verbal communication skills or behaviors selected from the database of target communication behaviors and skills, (b) generating a display of an application lesson for presentation to the user to elicit the desired user response, the application lesson including a visual schedule comprising a set of pictures that communicate a series of activities or steps of an activity, (c) displaying the application lesson to the user on the image display, including requesting the user to perform an activity or step from the visual schedule, (d) receiving from the sensor apparatus a user response, the user response including holding a picture element identifying the activity or step of the visual schedule for imaging by the sensor apparatus, (e) comparing the user response via the output from the sensor apparatus with the desired user response, including identifying the activity or step on the picture element of the visual schedule held by the user, (f) performing feedback analysis to determine the effect of the lesson, including initiating a specific action or lesson in response to identification of the activity or step on the picture element of the visual schedule held by the user, (g) generating a second display on the image display for presentation to the user to elicit the desired user response;

(h) tracking progress in multiple behaviors and skills as mastered by the user;

(i) chaining mastered behaviors and skills together into a more complex behavior or skill from the series of activities or steps of an activity of the visual schedule; and (j) displaying the more complex behavior or skill to the user, including requesting the user to perform a further activity or step from the visual schedule.

18. The system of claim 17, further including a reinforcement module operative to select and present a positive mode of reinforcement including a gesture game, visual content, audio content, verbal praise, and a preferred activity.

19. The system of claim 17, further including:

(j) reintroducing a mastered skill, behavior, or lesson to the user.

* * * * *